United States Patent

Michiels et al.

[11] Patent Number: 6,025,546
[45] Date of Patent: Feb. 15, 2000

[54] METHOD TO OBTAIN MALE STERILE PLANTS

[75] Inventors: Frank Michiels; Johan Botterman; Marc Cornelissen, all of Gent, Belgium

[73] Assignee: Plant Genetic System, N.V., Belgium

[21] Appl. No.: 08/894,440

[22] PCT Filed: Feb. 21, 1996

[86] PCT No.: PCT/EP96/00722

§ 371 Date: Nov. 12, 1997

§ 102(e) Date: Nov. 12, 1997

[87] PCT Pub. No.: WO96/26283

PCT Pub. Date: Aug. 29, 1996

[30] Foreign Application Priority Data

Feb. 21, 1995 [EP] European Pat. Off. .............. 95400364

[51] Int. Cl.[7] .......................... C12N 15/82; C12N 15/55; C12N 15/31; A01H 5/00; A01H 1/02
[52] U.S. Cl. ..................... 800/303; 800/274; 800/275; 800/285; 800/286; 800/287; 800/298; 800/306; 800/320.1; 800/320.2; 435/199; 435/419; 435/468
[58] Field of Search .................................. 800/274, 275, 800/285, 286, 287, 298, 303, 306, 320.1, 320.2; 435/199, 419, 468

[56] References Cited

U.S. PATENT DOCUMENTS 5,689,041  11/1997  Mariani et al. .......................... 800/205

FOREIGN PATENT DOCUMENTS 537 399   4/1993  European Pat. Off. .
91/09957  7/1991  WIPO .
92/13957  8/1992  WIPO .
92/21757  12/1992  WIPO .
93/08291  4/1993  WIPO .
93/10251  5/1993  WIPO .
93/19188  9/1993  WIPO .

OTHER PUBLICATIONS

Fromm et al. Bio/Technology 8(9): 833–839, 1990.
Turgut et al. Plant Mol. Biol. 24(1): 97–104, 1994.
An et al. Plant Physiol. 88(3): 547–552, 1988.

Primary Examiner—David T. Fox
Attorney, Agent, or Firm—Burns, Doane, Swecker & Mathis, L.L.P.

[57] ABSTRACT

A plant having in the nuclear genome of its cells foreign DNA comprising a male-sterility gene comprising:
  a male-sterility DNA encoding a sterility RNA, protein or polypeptide which, when produced or overproduced in a stamen cell of the plant, significantly disturbs the metabolism, functioning and/or development of the stamen cell, and,
  a sterility promoter directing expression of the male-sterility DNA selectively in specific stamen cells of said plant, the male-sterility DNA being in the same transcriptional unit as, and under the control of, the sterility promoter, and
a coregulating gene comprising:
  a coregulating DNA encoding a coregulating RNA, protein or polypeptide which is capable, when produced in plant cells wherein said sterility RNA, protein or polypeptide is produced, of sufficiently preventing the activity of said sterility RNA, protein or polypeptide,
whereby said coregulating DNA is in a transcriptional unit which is different from the transcriptional unit of said sterility DNA.

40 Claims, No Drawings

METHOD TO OBTAIN MALE STERILE PLANTS

This application is a 371 of PCT/EP96/00722 filed Feb. 21, 1996.

BACKGROUND OF THE INVENTION (i) Field of the Invention

The present invention relates to an improved method to obtain male-sterile plants using foreign male-sterility genes that comprise plant promoters that direct expression of a male-sterility DNA in stamen cells, and to plants obtained by the method.

(ii) Description of Related Art

In many, if not most plant species, the development of hybrid cultivars is highly desired because of their generally increased productivity due to heterosis: the superiority of performance of hybrid individuals compared with their parents (see e.g. Fehr, 1987, Principles of cultivar development, Volume 1: Theory and Technique, MacMillan Publishing Company, New York; Allard, 1960, Principles of Plant Breeding, John Wiley and Sons, Inc.).

The development of hybrid cultivars of various plant species depends upon the capability to achieve almost complete cross-pollination between parents. This is most simply achieved by rendering one of the parent lines male sterile (i.e., bringing them in a condition so that pollen is absent or nonfunctional) either manually, by removing the anthers, or genetically by using, in the one parent, cytoplasmic or nuclear genes that prevent anther and/or pollen development (for a review of the genetics of male sterility in plants see Kaul, 1988, 'Male Sterility in Higher Plants', Springer Verlag).

For hybrid plants where the seed is the harvested product (e.g., corn, oilseed rape) it is in most cases also necessary to ensure that fertility of the hybrid plants is fully restored. In systems in which the male sterility is under genetic control this requires the existence and use of genes that can restore male fertility. The development of hybrid cultivars is mainly dependent on the availability of suitable and effective sterility and restorer genes.

Endogenous nuclear loci are known for most plant species that may contain genotypes which effect male sterility, and generally, such loci need to be homozygous for particular recessive alleles in order to result in a male-sterile phenotype. The presence of a dominant 'male fertile' allele at such loci results in male fertility.

Recently it has been shown that male sterility can be induced in a plant by providing the genome of the plant with a chimeric male-sterility gene comprising a DNA sequence (or male-sterility DNA) coding, for example, for a cytotoxic product (such as an RNase) and under the control of a promoter which is predominantly active in selected tissue of the male reproductive organs. In this regard stamen-specific promoters, such as the promoter of the TA29 gene of Nicotiana tabacum, have been shown to be particularly useful for this purpose (Mariani et al., 1990, Nature 347:737, European patent publication ("EP") 0,344,029). By providing the nuclear genome of the plant with such a male-sterility gene, an artificial male-sterility is locus is created containing the artificial male-sterility genotype that results in a male-sterile plant. Various stamen-specific promoters have been described (see e.g., WO 92/13956, WO 92/13957).

In addition it has been shown that male fertility can be restored to the plant with a chimeric fertility-restorer gene comprising another DNA sequence (or fertility-restorer DNA) that codes, for example, for a protein that inhibits the activity of the cytotoxic product or otherwise prevents the cytotoxic product to be active in the plant cells (EP 0,412,911). For example the barnase gene of *Bacillus amyloliquefaciens* codes for an RNase, the barnase, which can be inhibited by a protein, the barstar, that is encoded by the barstar gene of *B. amyloliquefaciens*. The barnase gene can be used for the construction of a sterility gene while the barstar gene can be used for the construction of a fertility-restorer gene. Experiments in different plant species, e.g., oilseed rape, have shown that a chimeric barstar gene can fully restore the male fertility of male sterile lines in which the male sterility was due to the presence of a chimeric barnase gene (EP 0,412,911, Mariani et al., 1991, Proceedings of the CCIRC Rapeseed Congress, Jul. 9–11, 1991, Saskatoon, Saskatchewan, Canada; Mariani et al., 1992, Nature 357:384). By coupling a marker gene, such as a dominant herbicide resistance gene (for example the bar gene coding for phosphinothricin acetyl transferase (PAT) that converts the herbicidal phosphinothricin to a non-toxic compound [De Block et al., 1987, EMBO J. 6:2513]), to the chimeric male-sterility and/or fertility-restorer gene, breeding systems can be implemented e.g. to select for uniform populations of male sterile plants (EP 0,344,029; EP 0,412,911).

Barnase is an extracellular ribonuclease produced by *Bacillus amyloliquefaciens*. Barstar is an inhibitor of barnase that is produced intracellularly by the same bacterium to protect it from the toxic effects of the intracellular barnase activity (Hartley, 1989, TIBS, 14:450–454). Initial attempts to clone the barnase gene in *E.coli* and *B.subtilis* under control of its own or another bacterial promoter were unsuccesful as the produced barnase proved to be toxic to the host cells. When the bamase gene was reconstructed from previously cloned parts on the same plasmid as the barstar gene, the lethal effects of barnase expression were suppressed (Hartley, 1988, J. Mol. Biol. 202:913–915).

Whenever barnase is cloned in a bacterial host cell, such as *E.coli*, it may be useful to have the barstar gene, under control of its native or another bacterial promoter, present in the host cell to prevent possible harmful effects of undesired barnase expression. Paul et al, 1992, Plant Mol. Biol. 19:611–622 for instance, constructed a chimeric barnase gene under control of a tapetum specific promoter of the A9 gene of Arabidopsis. Plasmids pWP127 and pWP128 contain a DNA fragment encoding barstar and the mature barnase cloned between the 1437 bp A9 promoter fragment and a CaMV polyadenylation sequence. The promoter and coding sequence of barstar were included on these plasmids since mature barnase could not be cloned in its absence in *E.coli*.

As indicated above barnase DNA has been used to induce male-sterility in plants. However, other uses of barnase have also been described. WO 92/21757 describes inter alia a plant transformed with a nematode-induced chimaeric gene comprising the following operably linked DNA sequences:

a nematode-induced promoter that is suitable to direct transcription of a foreign DNA substantially selectively in specific root cells, preferably in the cells of fixed-feeding sites of the plant; and, a first foreign DNA that encodes barnase;

and which also contains a restorer chimaeric gene, preferably in the same genetic locus as the nematode-induced chimaeric gene, comprising the following operably linked DNA sequences:

a second promoter, such as a nematode-repressed promoter, which can direct transcription of a second foreign DNA in cells of the plant where the first foreign DNA is expressed, preferably substantially selectively in cells other than the specific root cells, preferably in cells other than the fixed feeding site cells, of the plant, and, a second foreign DNA that encodes barstar.

WO 93/19188 describes inter alia a plant transformed with a fungus-responsive chimaeric gene comprising the following operably linked DNA sequences:

a fungus-responsive promoter that is suitable to direct transcription of a foreign DNA substantially selectively in cells of a plant surrounding, preferably immediately surrounding, a site of infection of the plant by a fungus; and, a first foreign DNA that encodes barnase;

and which also contains a restorer chimaeric gene, preferably in the same genetic locus as the fungus-responsive chimaeric gene, comprising the following operably linked DNA sequences:

a second promoter, such as a constitutive promoter (e.g., 35S), which can direct transcription of a second foreign DNA in cells of the plant other than those surrounding, preferably in at least cells of the plant other than those immediately surrounding, said fungus infection site; and, a second foreign DNA that encodes barstar.

A foreign DNA, when introduced in the plant genome appears to integrate randomly in the plant genome. Examination of independently transformed plants has shown a high degree of variability (up to 100-fold) in the expression level of the introduced gene. Several studies have shown no correlation between this "between-transformant variability" and the copy number of the introduced DNA at a given locus. It has been suggested that some of the variability in expression of introduced genes in transgenic plants is a consequence of "position effects" caused by influences of adjacent plant genomic DNA. Other factors that could contribute to the variability in expression are physiological variability of the plant material, differences in the number of independent T-DNA loci in different transformants or the inhibitory effects of certain T-DNA structures on gene expression. Between-transformant variability in expression has been observed for the majority of introduced genes in transgenic plants. The variability in expression of many introduced genes in independent transgenic plants necessitates large numbers of transgenic plants to be assayed to accurately quantitate the expression of the gene. It would be of great importance if the amount of between-transformant variability could be reduced (Dean et al, 1988, NAR 16:9267–9283).

SUMMARY OF THE INVENTION

The invention concerns a plant having in the nuclear genome of its cells foreign DNA comprising:

a male-sterility gene comprising:

a male-sterility DNA encoding a sterility RNA, protein or polypeptide which, when produced or overproduced in a stamen cell of the plant, significantly disturbs the metabolism, functioning and/or development of the stamen cell, and, a sterility promoter directing expression of the male-sterility DNA selectively in specific stamen cells, especially in anther cells, particularly in tapetum cells, of the plant, the male-sterility DNA being in the same transcriptional unit as, and under the control of, the sterility promoter; and a coregulating gene comprising:

a coregulating DNA encoding a coregulating RNA, protein or polypeptide which is capable, when produced in plant cells wherein the sterility RNA, protein or polypeptide is produced, of sufficiently preventing the activity of the sterility RNA, protein or polypeptide, and preferably a promoter directing expression of said coregulating DNA in non-stamen cells, preferably at least in the majority of non-stamen cells, while directing low-level expression, preferably not directing expression, in said specific stamen cells, or a promoter consisting of a minimal promoter element, preferably of a promoter normally expressed in plant cells, particularly whereby said coregulating DNA is under control of enhancer elements in the nuclear genome of said plant, whereby the coregulating DNA is in a transcriptional unit which is different from the transcriptional unit of the sterility DNA.

This invention also provides a method to obtain male-sterile plants which comprises:

transforming the nuclear genome of plant cells with a foreign DNA comprising a male-sterility gene comprising:

a male-sterility DNA encoding a sterility RNA, protein or polypeptide, preferably barnase or a variant thereof, which, when produced or overproduced in a stamen cell of the plant, significantly disturbs the metabolism, functioning and/or development of the stamen cell, and, a sterility promoter capable of directing expression of the male-sterility DNA selectively in specific stamen cells, especially in anther cells, particularly in tapetum cells, of said plant, the male-sterility DNA being in the same transcriptional unit as, and under the control of, the sterility promoter, and regenerating plants transformed with said foreign DNA from said transformed cells, which method is characterized by including in said foreign DNA a coregulating gene comprising a coregulating DNA encoding a coregulating RNA, protein or polypeptide, preferably barstar, which is capable, when produced in plant cells wherein said sterility RNA, protein or polypeptide is produced, of sufficiently preventing the activity of said sterility RNA, protein or polypeptide, said coregulating DNA preferably being under the control of a promoter including:

a promoter capable of directing expression of said coregulating DNA in non-stamen cells, preferably at least in the majority of non-stamen cells, while directing low-level expression, preferably not directing expression, in said specific stamen cells, a promoter consisting of a minimal promoter element, preferably of a promoter normally expressed in plant cells, particularly whereby said coregulating DNA is capable of being placed under control of enhancer elements in the nuclear genome of said plant after integration of said foreign DNA in said plant genome, whereby said coregulating DNA is in a plant transcriptional unit which is different from the plant transcriptional unit of said sterility DNA, and provided that, when said coregulating DNA is not under control of a promoter capable of directing expression in plant cells, said coregulating gene is located in said foreign DNA in such a way that after insertion in the plant genome, the coregulating DNA is capable of being placed under the control of plant promoter sequences present in the DNA surrounding said foreign DNA in said plant genome.

The present invention further provides plants that contain in their nuclear genome said male-sterility gene and said coregulating gene, preferably in the same genetic locus.

DETAILED DESCRIPTION OF PREFERRED EMBODIMENTS

A male-sterile plant is a plant of a given plant species which is male-sterile due to expression of a male-sterility genotype such as a foreign male-sterility genotype containing a male-sterility gene. A restorer plant is a plant of the same plant species that contains within its genome at least one fertility-restorer gene that is able to restore the male fertility to a line of male-sterile plants containing a male-sterility genotype i.e. in those offspring obtained from a cross between a male-sterile plant and a restorer plant and containing both a male-sterility genotype and a fertility-restorer gene. A restored plant is a plant of the same species that is male-fertile and that contains within its genome a male-sterility genotype and a fertility-restorer gene.

A line is the progeny of a given individual plant.

A gene as used herein is generally understood to comprise at least one DNA region coding for an RNA, which may or may not be capable of being translated into a protein or polypeptide, which is operably linked to regulatory sequences that control the transcription of the DNA region. Such regulatory sequences include promoter regions, enhancer sequences and 3' regulatory sequences. A structural gene is a gene whose product is e.g., an enzyme, a structural protein, tRNA or rRNA A regulatory gene is a gene which encodes a protein which regulates the expression (e.g., the transcription) of one or more structural or other regulatory genes.

For the purpose of this invention the expression of a gene (or of a DNA of the gene which encodes the RNA), such as a chimeric gene, means that the DNA region of the gene coding for the RNA is transcribed, under control of the promoter and other regulatory sequences of the gene, into a RNA which is biologically active i.e., which is either capable of interacting with another RNA, or which is capable of being translated into a biologically active polypeptide or protein.

The expression of most eucaryotic genes, including foreign (e.g., chimeric) genes, is regulated by combination of a minimal promoter element and one or more enhancer elements which bind to regulatory proteins. When a promoter directs expression of any DNA it is active. Depending on the amount of RNA produced by a promoter under a given set of conditions one can speak about low or high level of expression (or less or high activity of the promoter). With regard to the present invention a "high" level of expression of the malesterility gene is interpreted as the level of expression in specific stamen cells whereby the production of fertile male gametes is prevented.

A minimal promoter element as used herein means a DNA that has the capacity to bind RNA polymerase and to initiate transcription. For any given gene the minimal promoter extends about 30–40, maximally 100, basepairs upstream from the transcription initiation site and generally includes the TATA box. An enhancer element is a regulatory element that is generally further upstream from the minimal promoter and that activates (or inhibits) transcription from the minimal promoter linked to it, with synthesis beginning at the normal start site. An enhancer is capable of binding transcription factors and can usually operate in both orientations and can function even when moved more than 1000 basepairs from the promoter and from either an upstream or a downstream position.

A promoter as used herein comprises a minimal promoter associated with one or more enhancer elements. For practical purposes a promoter and minimal promoter, as used herein, may also comprise part of the DNA that is transcribed (e.g., the untranslated leader of a mRNA).

A transcriptional unit means a DNA segment that is transcribed into a continuous RNA from a promoter. For the purposes of this invention a transcriptional unit comprises the promoter.

A promoter which directs expression selectively in specific cells or tissues of a plant (e.g., stamen cells such as tapetum cells) is a promoter in which the enhancer elements operate to limit the transcription to specific cells or tissues in the plant and/or to specific stages of development of these specific cells or tissues, i.e., to enhance transcription in the specific cells or tissues at particular developmental stages and to inhibit transcription in all other cells or tissues or at other developmental stages. For all practical purposes such selective promoters are specific in activity and effect. Usually such selective promoters are identified by differential screening of mRNA libraries from different tissues (Sambrook et al., 1989, "Molecular Cloning: a Laboratory Manual", Cold Spring Harbor Laboratory, and Ausubel et al, 1994, "Current Protocols in Molecular Biology", John Wiley & Sons). Although it is generally impossible to screen all tissues and all cells of a plant, promoters obtained in this way have been found to be useful to direct expression of heterologous DNA selectively in the same tissues in transgenic plants of the same and/or different plant species.

As used herein stamen cells will mean cells of at least one part of the male reproductive organ in a flower, in various stages of development, such as the filament, the anther, the tapetum, the anther cell wall, the pollen etc. A stamen-specific promoter is a promoter that is capable of directing expression (e.g., of barnase DNA) selectively in stamen cells (preferably including at least tapetum cells) at one or more stages in the development of the stamen to prevent the production of fertile pollen. It should be noted that a male-sterility gene comprising a pollen-specific promoter, i.e., a promoter that directs expression exclusively in microspores and/or pollen (i.e., after meiosis), when operably linked to a barnase DNA can only induce male-sterility in a plant when it is present in a homozygous form in the nuclear genome of that plant.

Non-stamen cells as used herein means all cells of a plant except the stamen cells (particularly the tapetum cells), especially those stamen cells in which the sterility promoter can direct expression of the barnase DNA.

The phenotype is the external appearance of the expression (or lack of expression) of a genotype i.e., of a gene or set of genes (e.g., male-sterility, presence of protein or RNA in specific plant tissues etc.).

As used herein, a genetic locus is a DNA (e.g., one or more genes) as defined with respect to its position in the nuclear genome, i.e., in a particular chromosome, of a plant. Two loci can be on different chromosomes and will segregate independently. Two loci can be located on the same chromosome and are then generally considered as being linked (unless sufficient recombination can occur between them).

An endogenous locus is a locus which is naturally present in a plant species. A foreign locus is a locus which is formed in the plant because of the introduction, e.g., by means of genetic transformation, of a foreign DNA. If a foreign DNA, which comprises two or more genes, is introduced in the plant genome this will generally be regarded as creating, in the plant genome, one foreign locus which comprises the two or more genes (although it can also be said that two or more closely linked loci are created).

In diploid plants, as in any other diploid organisms, two copies of a gene are present at any autosomal locus. Any gene can be present in the nuclear genome in several variant states designated as alleles. If two identical alleles are present at a locus that locus is designated as being homozygous, if different alleles are present, the locus is designated as being heterozygous. The allelic composition of a locus, or a set of loci, is the genotype. Any allele at a locus is generally represented by a separate symbol (e.g., M and m, S and -, - representing the absence of the gene). A foreign locus is generally characterized by the presence and/or absence of a foreign DNA A dominant allele is generally represented by a capital letter and is usually associated with the presence of a biologically active gene product (e.g., a protein) and an observable phenotypic effect.

A plant can be genetically characterized by identification of the allelic state of at least one genetic locus.

The genotype of any given locus can be designated by the symbols for the two alleles that are present at the locus (e.g., M/m or m/m or S/-). The genotype of two unlinked loci can be represented as a sequence of the genotype of each locus (e.g., S/S, R/-)

Foreign male-sterility loci are those in which the allele responsible for male sterility is a foreign DNA sequence S which comprises the male-sterility gene which when expressed in cells of the plant renders the plant male-sterile without otherwise substantially affecting the growth and development of the plant.

The male-sterility locus preferably also comprises in the same genetic locus at least one marker gene T which comprises at least:

t1) a marker DNA encoding a marker RNA, protein or polypeptide which, when present at least in a specific tissue or specific cells of the plant, renders the plant easily separable from other plants which do not contain the marker RNA, protein or polypeptide encoded by the marker DNA at least in the specific tissue or specific is cells, and, t2) a marker promoter capable of directing expression of the marker DNA at least in the specific tissue or specific cells: the marker DNA being in the same transcriptional unit as, and under the control of, the marker promoter.

Such male-sterility gene is always a dominant allele at such a foreign male-sterility locus. The recessive allele corresponds to the absence of the male-sterility gene in the nuclear genome of the plant.

Male-sterility DNAs and sterility promoters that can be used in the male-sterility genes of this invention have been described before (EP 0,344,029 and EP 0,412,911). For the purpose of this invention the expression of the male-sterility gene in a plant cell should be able to be inhibited or repressed for instance by means of expression of a suitable fertility-restorer gene in the same plant cell. In this regard a particular useful male-sterility DNA codes for barnase (Hartley, J.Mol. Biol. 1988 202:913). The sterility promoter can be any promoter but it should at least be active in stamen cells, particularly tapetum cells. Particularly useful sterility promoters are promoters that are selectively active in stamen cells, such as the tapetum-specific promoters of the TA29 gene of *Nicotiana tabacum* (EP 0,344,029) which can be used in tobacco, oilseed rape and other Brassica species, chicory, corn, rice, wheat and other plant species; the PT72, the PT42 and PE1 promoters from rice which can be used in rice, corn, wheat, and other plant species (WO 92/13956); the PCA55 promoter from corn which can be used in corn, rice, wheat and other plant species (WO 92/13957); and the A9 promoter of a tapetum-specific gene of *Arabidopsis thaliana* (Paul et al., 1992, Plant Mol. Biol. 19:611–922).

It has been found that stamen-specific promoters, such as PTA29, operably linked to a suitable sterility DNA, such as the barnase DNA, can be used in a variety of plant species to induce male-sterility. Indeed, by transformation of plants with such male-sterility genes, male-sterile lines with high agronomic value have been obtained in many plant species. Apparently, the stamen-specific promoters, for all practical purposes, substantially retain their spatial and temporal specificity. However, not all individual transformed plants can be developed into lines with good agronomical performance. Indeed some plants show undesired phenotypic effects which can be due to somaclonal variation and/or 'position effects'. It is believed that at least part of this variation is due to the regulating effects of native (i.e., endogenous) enhancer elements in the plant genome that surround the integrated male-sterility gene in the transgenic plants. Such enhancer sequences, and consequently their effects on the expression of the male-sterility gene, differ depending on the place of integration of the male-sterility gene. This can result, in some transformants, in low-level (often even undetectable) expression of the sterility DNA (e.g., barnase DNA) in tissues other than the stamen cells, e.g., in cells during tissue culture or in somatic cells of the plants or seeds.

In this regard, this invention is based on the observation that, under some circumstances, a chimeric gene such as the barstar gene, introduced together with a male-sterility gene such as a gene comprising barnase DNA can decrease the between-transformant variability in expression of the male-sterility gene, and of its resulting phenotype, and can increase the frequency of transformants having good agronomical performance. For the purposes of this invention it is therefore preferred that the sterility DNA is the barnase DNA while the coregulating DNA is the barstar DNA.

For the purposes of this invention barnase DNA means a DNA coding for the ribonuclease of *Bacillus amyloliquefaciens* with the amino acid sequence as described by Hartley, 1988, J.Mol.Biol. 202:913915 (barnase s.s.) or any variants thereof which have ribonuclease activity and are capable of being inactivated by barstar. In this regard one of such variants of barnase s.s. has been found to be encoded by the DNA of *Bacillus intermedius* which encodes a ribonuclease (binase) which has 84% identity at the amino acid level with barnase s.s. (Schulga et al, 1992, NAR 20:2375; see also Guillet et all, 1993, Structure 1:165–177). Preferably, the barnase variants retain at least 10% particularly at least 50% of the activity of barnase s.s. as measured under standard conditions (Fitzgerald and Hartley. 1993, Anal. Biochem. 214:544–547; Hartley et al, 1993, Biochemistry 32:5978–5984).

For the purposes of this invention barstar DNA means a DNA coding for an inhibitor of the barnase ribonuclease of *Bacillus amyloliquefaciens* as described by Hartley, 1988, J.Mol.Biol. 202:913–915 (barstar s.s.) or any variants thereof which are capable of inhibiting barnase s.s. In this regard one of such variants has been found to be encoded by the DNA *Bacillus intermedius* which encodes binstar (Guillet et al, 1993, Structure 1:165–177). Preferably the barstar variants are capable of inhibiting at least 90% of barnase activity, particularly at least 50% of barnase activity, in an equimolar mixture of the barstar variant and barnase in standard condition (Hartley et al, 1993, Biochemistry 32:5978–5984).

However, any DNA coding for a ribonuclease can be used as sterility DNA in this invention provided a DNA coding for protein inhibitor of that ribonuclease can be obtained. Examples of such RNAses and corresponding inhibitors are for instance listed in Guillet et al, 1993, Structure 1:165–177. Another example of such a ribonuclease is the RNAse Sa or sarnase of *Streptomyces aureofaciens* (Shlyapnikov et al, 1986, FEBS Letters 209:335–339; Homerova et al, 1992, Gene 119:147–148). An inhibitor of RNAse Sa is known (Mucha et al, 1983, Biologia 38:1177–1184).

Of course, any sterility DNA coding for a RNA, protein or polypeptide and its corresponding coregulating DNA coding for a coregulating RNA, protein or polypeptide which, when expressed in the same plant cell as the sterility DNA is capable of preventing expression of the sterility DNA or the activity of the sterility RNA, protein or polypeptide can be used. In this regard DNAs that are described as fertility restorer DNAs in EP 0,412,911 can be used as coregulating DNAs of this invention in combination with their corresponding sterility DNAs which are also described in EP 0,412,911.

The promoter in the coregulating gene (the "coregulating promoter") of this invention is preferably capable of driving expression of the coregulating DNA (e.g., the barstar DNA) in a variety of cells and tissues, preferably all cells and tissues, of the plant to counteract the undesired effects of possible low level expression of the male-sterility gene (e.g., comprising the barnase DNA). In this regard, the promoter can also drive expression in those stamen cells in which the sterility promoter drives expression of barnase (as an example of a sterility DNA) and which are killed by the biological activity of the barnase which prevents the production of fertile male gametes. Of course in such stamen cells the activity of the sterility promoter and the coregulating promoter should be such that for instance the amount of produced barnase in such stamen cells is higher than that of the produced barstar at least during a period in stamen development. In this regard it is preferred that the coregulating promoter is not active in the same stamen cells as the sterility promoter. However, outside the stamen cells (e.g., the tapetum) in which the sterility promoter drives expression of the barnase DNA, the coregulating promoter may be active at any level. If the coregulating promoter is active in the same stamen cells as the sterility promoter (but so that sufficient barnase is still produced in the stamen cells to render the plant male-sterile) this can have the added advantage that the restoration of male fertility in the progeny of these male-sterile plants after crossing with restorer plants containing a fertility-restorer gene (e.g., comprising the barstar DNA under control of a stamen-specific promoter), is generally easier due to the fact that the amount of barnase in the stamen cells is already reduced due to expression of the coregulating gene.

Preferably the coregulating promoter is a promoter operable in plant cells and as such many promoters can be used in this invention. In a preferred embodiment the 35S promoter ("P35S") of the Cauliflower Mosaic virus is used. This is a family of promoters that are generally known as constitutive promoters but that appear to be relatively less active in anther cells, particularly in tapetum cells. Surprisingly it was found that the activity of the P35S is sufficiently low in tapetum cells and that it can be used together with a male-sterility gene comprising a tapetum-specific promoter. Even more surprisingly it was found that the use of the P35S as coregulating promoter was particularly effective in rice, especially when PT72 and pE1 are used as sterility promoters, and in corn, especially when PCA55 or PTA29 are used as sterility promoters.

Suitable P35S promoters can be obtained from the Cauliflower Mosaic Virus ("CaMV") isolates CM1841 (Gardner et al (1981) Nucl. Acids. Res. 9:2871) and CabbB-S (Franck et al (1980) Cell, 21:285) (the "35S2 promoter" or "P35S2"), from the CaMV isolate CabbB-JI (Hull and Howell (1978) Virology 86:482) (the "35S3 promoter" or "P35S3"). P35S3 differs from P35S2 in its sequence (the sequence of P35S3 is disclosed in European patent publication ("EP") 359617) and in its greater activity in transgenic plants (Harpster et al (1988) Mol. Gen. Genet. 212:182).

Of course other known constitutive promoters can be used as coregulating promoter. For instance the promoter of the nopaline synthase gene of Agrobacterium T-DNA ("Pnos") is known to drive low-level expression in a constitutive way in plants. It is believed that Pnos is particularly effective as coregulating promoter in dicot plants, such as Brassica species, e.g., *Brassica napus*.

Other suitable constitutive promoters that can be used as coregulating promoters are the TR1' and the TR2' promoters (resp. "PTR1" and "PTR2") which drive the expression of the 1' and 2' genes, respectively, of the T-DNA of Agrobacterium (Velten et al (1984) EMBO J. 3:2723), and are wound-induced promoters that are only weakly active in the uninduced state.

Suitable organ-specific, tissue-specific and/or inducible foreign promoters can also be used as coregulating promoters such as the promoters of the small subunit genes (such as the 1A gene) of 1,5-ribulose bisphosphate carboxylase of *Arabidopsis thaliana* (the "ssu" promoter) which are light inducible promoters (Krebbers et al (1988) Plant Mol. Biol. 11:745) active primarily in photosynthetic tissue; and the seed-specific promoters of, for example, *Arabidopsis thaliana* (Krebbers et al (1988) Plant Physiol. 87:859), and the promoter of the Kunitz trypsine inhibitor gene (Jofuku and Goldberg, 1989, The Plant Cell 1:1079–1093).

In another preferred embodiment of this invention the coregulating promoter comprises a minimal promoter element which can be derived from any promoter that can be expressed in plant cells including constitutive promoters (P35S, Pnos), tissue-specific promoters (PTA29, PCA55, PT72, PE1, PT42), or inducible promoters (e.g., PTR1, PTR2, Pssu). Such minimal promoter element is the sequence comprising about 30–50, maximally about 100 basepairs upstream from the transcription start site and which contains the TATA box.

Such a minimal promoter element can be used in the coregulating gene of this invention to direct low-level transcription of the barstar DNA in non-stamen cells.

In addition, the position effects in transgene expression can now be used to good effect. Indeed, the plant genomic DNA that is adjacent to the foreign DNA (or transgene) may comprise additional sequences, such as enhancer sequences, that are capable of regulating the minimal promoter to enhance transcription of the barstar DNA in a variety of plant cells. In this regard it is preferred that the coregulating gene is provided in a transforming DNA in such a way that especially upstream sequences are brought in optimal position to the minimal promoter. In this regard it is preferred that the coregulating gene is present at the extreme ends of the foreign DNA (e.g., the T-DNA).

The coregulating gene may even be lacking sequences required for being transcribed in a plant cell. For instance the coregulating gene may only comprise the coregulating DNA or it may comprise the coregulating DNA with upstream sequences that are not capable of directing expression of the coregulating DNA in plant cells. Thus the coregulating gene may lack a suitable promoter or it may comprise a bacterial promoter. (e.g., the native promoter of the barstar gene in *B amyloliquefaciens* or the tac promoter). However, in this instance, it is preferred that the coregulating gene is present at the extreme ends of the foreign DNA used for plant transformation (e.g., the T-DNA) in such an orientation that the translation initiation codon of the coregulating DNA is closest to one of the ends of the foreign DNA Indeed, it is believed that this orientation increases the probability that the coregulating gene, when inserted in the plant genome, is placed under control of (i.e., has "captured") suitable promoter (e.g., minimal promoters) and/or enhancer sequences in the adjacent plant genomic DNA to enable the more or less constitutive expression of the coregulating DNA such as the barstar DNA. Because it is unlikely that the plant promoter and/or enhancer sequences will be optimally positioned with respect to the barstar DNA, it is expected that the level of any expression of the barstar DNA will be very low, as desired in many cases.

The male-sterility gene and the coregulating gene are preferably inserted in the plant genome as a single transforming DNA Therefore both genes should preferably be present on the same vector or should be part of the same T-DNA.

However, both genes could also be present on separate DNAs which are both used for transformation. In such "cotransformation" it has been found that both DNAs are likely to be integrated in the same genetic locus of the plant genome, although there is of course a probability that both genes are integrated at different locations in the plant genome. In this respect the foreign DNA used for transformation of the nuclear genome of a plant cell need not be a single DNA molecule but can be multiple DNA molecules. For the purpose of the present invention it is however preferred that the male-sterility gene and the coregulating gene be integrated in the same locus in the plant nuclear genome.

However, if the coregulating gene is useful to counteract the low level expression of the male-sterility gene in tissue culture, its presence might not be required in the mature plants and their progeny. If the plants are transformed by cotransformation, and if the male-sterility gene and coregulating gene are integrated at different locations in the plant genome, then both genes will segregate in the progeny and the coregulating gene can hereby be removed from the transformed plant line.

The male sterile plants of this invention can be crossed with male-fertile parent plants, particularly a male-fertile restorer plant containing a suitable fertility restorer gene (see e.g., EP 0,412,911).

Marker DNAs and marker promoters that can be used in the marker gene as used in this invention are also well known (EP 0,344,029; EP 0,412,911).

Foreign DNA such as the male-sterility gene, the fertility-restorer gene, the coregulating gene, or the marker gene preferably also are provided with suitable 3' transcription regulation sequences and polyadenylation signals, downstream (i.e., 3') from their coding sequence i.e., respectively the fertility-restorer DNA, the male sterility DNA, the coregulating DNA or the marker DNA. In this regard either foreign or endogenous transcription 3' end formation and polyadenylation signals suitable for obtaining expression of the chimeric gene can be used. For example, the foreign 3' untranslated ends of genes, such as gene 7 (Velten and Schell (1985) Nucl. Acids Res. 13:6998), the octopine synthase gene (De Greve et al., 1982, J.Mol. Appl. Genet. 1:499; Gielen et al (1983) EMBO J. 3:835; lngelbrecht et al., 1989, The Plant Cell 1:671) and the nopaline synthase gene of the T-DNA region of *Agrobacterium tumefaciens* Ti-plasmid (De Picker et al., 1982, J.Mol. Appl. Genet. 1:561), or the chalcone synthase gene (Sommer and Saedler, 1986, Mol-.Gen.Genet. 202:429–434), or the CaMV 19S/35S transcription unit (Mogen et al., 1990, The Plant Cell 2:1261–1272) can be used.

The fertility-restorer gene, the male-sterility gene, the coregulating gene or the marker gene in accordance with the present invention are generally foreign DNAs, preferably foreign chimeric DNA In this regard "foreign" and "chimeric" with regard to such DNAs have the same meanings as described in EP 0,344,029 and EP 0,412,911.

The cell of a plant, particularly a plant capable of being infected with Agrobacterium such as most dicotyledonous plants (e.g., *Brassica napus*) and some monocotyledonous plants, can be transformed using a vector that is a disarmed Ti-plasmid containing the male-sterility gene and/or the coregulating gene (preferably both) and carried by Agrobacterium. This transformation can be carried out using the procedures described, for example, in EP 0,116,718 and EP 0,270,822. Preferred Ti-plasmid vectors contain the foreign DNA between the border sequences, or at least located to the left of the right border sequence, of the T-DNA of the Ti-plasmid. Of course, other types of vectors can be used to transform the plant cell, using procedures such as direct gene transfer (as described, for example, in EP 0,233,247), pollen mediated transformation (as described, for example, in EP 0,270,356, PCT patent publication "WO" 85/01856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536, 475). Cells of monocotyledonous plants such as the major cereals including corn, rice, wheat, barley, and rye, can be transformed. (e.g., by electroporation) using wounded or enzyme-degraded intact tissues capable of forming compact embryogenic callus (such as immature embryos in corn), or the embryogenic callus (such as type I callus in corn) obtained thereof, as described in WO 92/09696. In case the plant to be transformed is corn, other recently developed methods can also be used such as, for example, the method described for certain lines of corn by Fromm et al., 1990, Bio/Technology 8:833; Gordon-Kamm et al., 1990, Bio/Technology 2:603 and Gould et al., 1991, Plant Physiol. 95:426. In case the plant to be transformed is rice, recently developed methods can also be used such as, for example, the method described for certain lines of rice by Shimamoto et al., 1989, Nature 338:274; Datta et al., 1990, Bio/Technology 8:736; and Hayashimoto et al., 1990, Plant Physiol. 93:857.

The transformed cell can be regenerated into a mature plant and the resulting transformed plant can be used in a conventional breeding scheme to produce more transformed plants with the same characteristics or to introduce the male-sterility gene, the coregulating gene (or both), in other varieties of the same related plant species. Seeds obtained from the transformed plants contain the chimeric gene(s) of this invention as a stable genomic insert. Thus the male-sterility gene, and/or the coregulating gene of this invention when introduced into a particular line of a plant species can always be introduced into any other line by backcrossing.

The present invention thus provides a method to obtain male-sterile plants whereby the frequency of obtaining, from transformation, male-sterile plants with good agronomic performance is increased. This is because the coregulating gene is expressed in non-stamen cells. In this regard the presence of the coregulating gene may counteract a number of phenomena such as:

low-level expression of the male-sterility gene in some transformed plant cells in tissue culture, including regeneration prior to normal plant development. Indeed such tissue culture cells have a physiology and metabolism and patterns of gene regulation which may be different from that of any differentiated cell in a plant or seed. Since the sterility promoter is generally selected on the basis of its natural activity in the plant or seed, position effects are perhaps expected to be more pronounced to activate the promoter in tissue culture cells. When direct gene transfer is used an additional phenomenon may occur. Indeed in such transformation method a large amount of DNA is delivered to any recipient cell. If gene repression should be an active process, which requires for instance DNA methylation or repressor protein binding, the repression mechanism may become temporarily overloaded, and the delivered DNA may be expressed for a short period of time. It can be seen that the coregulating gene can thus increase the general transformation efficiency.

low-level expression of the sterility DNA (e.g., the barnase DNA) in specific non-stamen cells of the primary transformants and/or particularly the progeny plants obtained thereof. Such low level expression can be due to several factors many of which are largely unknown: activation of the stamen-specific promoter by elements in the vector used for transformation, position effects as outlined above. Such effects may possibly be more pronounced in plants with a small genome and little repetitive DNA, such as rice.

rearrangements in additional copies of the transgene. This is most likely to occur in transformation by direct gene transfer in which multiple copies of the transforming DNA are often integrated at the same genetic locus in the plant genome with subsequent rearrangements of some of the copies. During such rearrangements, a DNA containing barnase DNA could be inadvertently be placed under control of a promoter present in the transforming DNA (e.g., the P35S promoter) or in the adjacent plant genomic DNA.

Whatever the reason, the use in plant transformation of a coregulating gene of this invention combined with a corresponding male-sterility gene will generally result in a higher frequency of male-sterile transgenic plants with good agricultural performance.

It will also be appreciated that the coregulating genes of the invention will be useful in combination with a pseudo male-sterility gene which comprises a male-sterility DNA that is under control of promoters that are not entirely stamen-specific, but that also are known to direct expression in some other tissue(s) outside the stamen (e.g., seeds). In this regard the coregulating promoter should be a promoter that is active in these some other tissue(s) to a sufficient level to counter the expression of the pseudo male-sterility gene but that it does not prevent the pseudo male-sterility gene" to be expressed in stamen cells (e.g., tapetum, anther-epidermal cells). In this regard the pseudo male-sterility gene and the coregulating gene together will be equivalent to a male-sterility gene which comprises a true stamen-specific promoter. As already indicated, the invention allows the generation of a higher number of male-sterile plants with good agronomical performance. In such plants the male-sterility gene will be genetically stable, i.e., the gene should be inherited and all plants comprising the gene should be male-sterile. Nevertheless it may not be absolutely required that all seeds that contain the gene are viable (i.e., will grow into normal mature plants). It is generally sufficient that from each male-sterile plant viable seeds that have inherited the male-sterility gene can be obtained.

Preferably the performance of the male-sterility gene (i.e., its phenotypic expression) should also be independent on genetic background so that the gene can be readily introduced in other lines through backcrossing.

It is generally also required that the male-sterility genotype is environmentally stable and that the phenotype will be independent of the various environmental conditions that can occur in the area and period in which the plants will be grown. Such environmental stability is usually demonstrated by performing field trials with the male-sterile plants in 3 or 4 different locations.

It is generally also desired that the male-sterility genotype has no significant negative effects on agronomically important characteristics and on plant development Nevertheless this will depend not only on the performance of the male-sterile parent line, but also on the performance of the hybrid obtained from that parent line. Indeed, these negative effects can in some circumstances be compensated by significant advantages in the hybrid.

Finally, in plant species where restoration of fertility is required, either in maintenance of the male-sterile line, or in hybrid seed production, the male-sterility genotypes should be restorable by at least one fertility restorer gene.

Unless otherwise indicated all experimental procedures for manipulating recombinant DNA were carried out by the standardized procedures described in Sambrook et al., 1989, "Molecular Cloning: a Laboratory Manual", Cold Spring Harbor Laboratory, and Ausubel et al, 1994, "Current Protocols in Molecular Biology", John Wiley & Sons, Vols 1 and 2.

The polymerase chain reactions ("PCR") were used to clone and/or amplify DNA fragments. PCR with overlap extension was used in order to construct chimeric genes (Horton et al, 1989, Gene 77:61–68; Ho et al, 1989, Gene 77:51–59).

All PCR reactions were performed under conventional conditions using the Vent™ polymerase (Cat. No. 254L—Biolabs New England, Beverley, Mass. 01915, U.S.A) isolated from *Thermococcus litoralis* (Neuner et al., 1990, Arch.Microbiol. 153:205–207). Oligonucleotides were designed according to known rules as outlined for example by Kramer and Fritz (1987, Methods in Enzymology 154:350), and synthesized by the phosphoramidite method (Beaucage and Caruthers, 1981, Tetrahedron Letters 22:1859) on an Applied Biosystems 380A DNA synthesizer (Applied Biosystems B.V., Maarssen, Netherlands).

In the description and in the following examples, reference is made to the following sequence listing:

SEQUENCE LISTING

| SEQ ID NO 1: | pTS174 |
|---|---|
| SEQ ID NO 2: | pTS88 HindIII-EcoRI |
| SEQ ID NO 3: | pVE136-EcoRI-HindIII |
| SEQ ID NO 4: | T-DNA of pTCO113 |

EXAMPLES

Example 1
Coregulating Genes in Rice

Compact embryogenic callus from rice cultivar Kochihibiki was obtained and transformation of callus cells by electroporation was achieved using the procedures as described in WO 92/096096, particularly in Example 9, except that the transforming DNA consisted of either plasmid pTS174 or plasmids pTS174 and pTS88 in equimolar amounts or more preferably in a 1:3 molar ratio. Prior to transformation, pTS174 and pTS88 were preferably linearized by digestion with appropriate restriction enzymes. All tissue culture steps were also carried out as decribed in WO 92/09696, example 9.

pTS174 is a pUC19 derived plasmid containing, in its polylinker, the barnase DNA under control of the PE1 promoter (PE1-barnase-3'nos) and the bar gene under control of a 35S promoter (P35S-bar-3'g7). The sequence of pTS174 is given in SEQ ID No 1. pTS88 is a pGEM2 derived plasmid containing, between the HindIII and EcoRI sites of its polylinker, the barstar DNA under control of a 35S promoter (P35S-barstar-3'g7). The sequence of the HindIII-EcoRI fragment of pTS88 is given in SEQ ID No 2. All chimeric genes comprising barstar, barnase, or bar also contained suitable 3' untranslated regions (e.g., of the nopaline synthase gene (3'nos) and gene 7 (3'g7) of Agrobacterium T-DNA).

Plasmids containing a fertility restorer gene comprising the barstar DNA under control of stamen-specific promoter of rice (PE1-barstar), and a herbicide resistance gene comprising the bar gene under control of the 355 promoter (P35S-bar) chimeric genes were used as control.

The results of the transformation experiments are presented in Table 1. In transformation experiments with pTS174 only one normal male-sterile line could be recovered from 48 electroporation cuvettes. In transformation experiments with PTS174+pTS88, 7 normal male sterile lines could be recovered from 40 cuvettes. Each cuvette contained about 50 callus pieces (approximately 1–2 mm in diameter) of tissue fragments.

In this regard a normal male-sterile plant is understood to be a male-sterile rice plant (i.e., with small, white anthers that do not contain pollen) that is, otherwise completely normal (e.g., is female-fertile) and that transmits the male-sterility phenotype to its progeny in accordance with normal Mendelian segregation of the chimeric barnase gene.

From table 1 it is also clear that the advantage of using pTS174+pTS88 over using pTS174 alone resides in the number of normal regenerated shoots that can be recovered on selective regeneration medium thus attesting to the fact that the P35S-barstar gene affects mainly cells in tissue culture. In this regard it is also important to note that plants containing both the P35S-barstar-3'g7 and the PE1-barnase-3'nos chimeric genes are male-sterile attesting to the fact that the P35S promoter is not active (or less active than the PE1 promoter) in specific stamen cells (particularly tapetum cells) of rice plants.

Example 2
Coregulating Genes in Corn.

Maize plants of lines H99, Pa91 and (Pa91×H99)×H99 ((P×H)×H) were grown in the greenhouse. Type I callus was initiated from immature zygotic embryos of 1 to 1.5 mm in size, which were excised from ears 10 to 14 days after pollination and then plated on MahIVII callus initiation medium (D'Halluin et al, 1992, The Plant Cell 4:1495–1505). Embryogenic callus was removed from the scutella of the embryos and subcultured every 2 to 3 weeks on Mah1VII substrate. Pieces of embryogenic tissue (about 1 to 1.5 mm in diameter) were isolated from actively growing embryogenic callus cultures and were placed on a plate with MahIVII substrate supplemented with 0.2 M mannitol and 0.2 M sorbitol for osmotic pretreatment for 4 hours before bombardment (Vain et al, 1993, Plant Cell Reports 12:84–88). A total amount of about 250 mg of tissue per plate was used in the bombardment experiments. DNA was bombarded into the tissue using the PDS-1000/He Biolistics® device (Bio-Rad). Microcarrier preparation and coating of DNA onto the microcarriers was essentially as described by Sanford et al (1993, In Wu, R. (Ed.). Meth. Enzymol. 217:483–509). The particle bombardment parameters were: target distance: 6 to 9 cm; bombardment pressures: 1100 to 1500 psi; gap distance: ¼ inches; macrocarrier flight distance: 11 mm. DNA was either linear or circular. The bombarded tissue was removed from the high osmotic medium (between 0 to 24 hours after bombardment) and transferred to selective maintenance medium without caseine hydrolysate and proline, but containing 10 to 20 mg/l BASTA The embryogenic callus was subcultured every 2 to 3 weeks for a total period of 6 to 8 weeks and was then transferred to MS medium (Murashige and Skoog, 1962, Physiol. Plant. 15:473–497) containing 3% sucrose, 10–20 mg/l BASTA, and 5 mg/l BAP (for lines H99) or 5 mg/l zeatine (for lines Pa91 or (P×H)×H). The embryogenic tissue was subcultured twice on substrate containing the appropriate cytokinin. Small regenerating plants were recovered and transferred to MS medium without hormones, but containing 6% sucrose and 10–20 mg/l BASTA Further developing shoots were transferred to half-strength MS medium with 1.5% sucrose for further elongation. The resulting plantlets were then transferred to soil in the greenhouse. It was found that after the transformation step, the concentration of BASTA in the culture medium could be reduced down to 2 mg/l.

The following DNA was used. In one set of experiments callus was transformed with plasmid pVE136 which is a pUC19 derived plasmid containing, between the EcoRI and HindIII sites of its polylinker, the barnase DNA under control of the PCA55 promoter (PCA55-barnase-3'nos) and a chimeric P35S-bar-3'nos gene. The sequence of the EcoRI-HindIII fragment of pVE136 is given in SEQ ID. No. 3. In other experiments callus was bombarded with an equimolar mixture of pVE136 and pTS88. pTS88 is the plasmid described in Example 1. In control experiments callus was bombarded with plasmid pDE110 which is a plasmid containing only the P35S-bar-3'nos chimeric gene and is described in WO 92/29696.

The results of the transformation experiments are presented in Table 2. In transformation experiments with pVE136+pTS88 the number of PAT positive plants, relative to the starting material, is almost twice that obtained in experiments using pVE136 alone.

It is important to note that corn plants containing both the P35S-barstar-3'g7 and the PCA55-barnase-3'nos chimeric genes are male-sterile attesting to the fact that the P35S promoter is not active (or less active than the PCA55 promoter) in stamen cells of corn plants.

Example 3

Coregulating Genes in Oilseed Rape

Oilseed rape plants (Brassica napus—both spring and winter varieties) were transformed with plasmid pTCO113 using the Agrobacterium mediated transformation procedure essentially as decribed by De Block et al, 1989, Plant Physiol. 91:694–701.

Plasmid pTCO113 is a intermediate cloning vector (T-DNA vector) containing between Agrobacterium T-DNA borders the following genes:

the bar gene under control of the PSSU promoter the barnase gene under control of the PTA29 promoter the barstar gene under control of the Pnos promoter.

The sequence of the T-DNA of pTCO113 is presented in SEQ ID. No 4.

Transformation efficiency with pTCO113 was observed to be equal to that obtained with pTHW107 which is a T-DNA vector that is identical to pTCO113 but lacks the Pnos-barstar gene (the nucleotide sequence of pTHW107 is identical to that of SEQ ID No. 4 except that it lacks the nucleotide region 4917–5834).

Oilseed rape plants transformed with pTCO113 were observed to be male-sterile. More precisely, of 31 spring oilseed rape plants regenerated after transformation with pTCO113, 27 plants (87%) were shown to be male-sterile. Of 22 spring oilseed rape plants regenerated after transformation with pTHW107, 20 plants (91%) were shown to be male-sterile (Table 3).

Seeds harvested from malesterile TO plants pollinated by untransformed male-fertile plants, were grown into T1 plants in the greenhouse. 50% of the plants of each T1 line are expected to carry the male-sterility gene. Plants were analyzed at the time that 50%, respectively 100% of the plants had started flowering. It was observed that plants transformed with pTCO113 have a smaller delay of flowering as compared to plants transformed with pTHW107. This was measured by the ratio of male-fertile (F)/male-sterile (S) plants at the moment that 50% of the plants had started to flower (Table 3). When all plants flowered, the ratio F/S was 54/46 for both pTCO113 and pTHW107 plants.

The seeds harvested from male-sterile T1 plants of different lines, pollinated by untransformed male-fertile plants, were sown in the field and analyzed with respect to the segregation of the male-sterility genes in the T2 progeny plants. Only 2 out of 7 tested pTHW107 lines, but no less than 12 out of 14 tested pTCO113 lines, showed a normal 1:1 Mendelian segregation ($X^2=6.86$, $p<0.01$) (Table 3).

It can therefore be conducted that in transformation experiments with pTCO113 a higher percentage of good male-sterile plants was obtained.

TABLE 1

| DNA | Total Nr of cuvettes (Nr of experiments) | Regenerants | | | |
|---|---|---|---|---|---|
| | | PAT+[1] normal shoots | PCR+[2] | male-sterility phenotype[3] | progeny analysis[4] |
| pTS174 | 48 (9) | 1 | 1/1 | 1/1 | 1/1 |
| pTS174 + pTS88 | 40 (8) | 33 | 24/33 | 9/24 | 7/9 |

TABLE 1-continued

| DNA | Total Nr of cuvettes (Nr of experiments) | Regenerants | | | |
|---|---|---|---|---|---|
| | | PAT+[1] normal shoots | PCR+[2] | male-sterility phenotype[3] | progeny analysis[4] |
| FR constructs | 23 (9) | 23 | — | — | — |

[1]Total number of shoots regenerated on PPT (i.e., selective) medium that appeared phenotypically normal
[2]Number of PCR+ plants/Number of analyzed PAT+ plants. PCR+ for barnase or barnase/barstar.
[3]Number of male-sterile but otherwise normal plants/number of analyzed barnase PCR+ plants
[4]Number of phenotypically normal male-sterile plants with good segregation of male-sterile phenotype in progeny/Nr of analyzed male-sterile plants

TABLE 2

| DNA | Total Nr of bombarded plates | Regenerants | | | |
|---|---|---|---|---|---|
| | | PAT+[1] | PCR+[2] barnase | male-sterility phenotype[3] | Progeny analysis[4] |
| pVE136 | 118 | 68[5] | 34/62 | 27/34 | 7/16 |
| pVE136 + pTS88 | 131 | 141 | 82/125 | 64/82 | 17/34 |
| pDE110[6] | 65 | 125 | — | — | — |

[1]Total number of PAT+ regenerants recovered from all transformation experiments.
[2]Number of PCR+ plants/Number of analyzed PAT+ plants
[3]Number of male-sterile plants/number of analyzed barnasePCR+ plants
[4]Number of male-sterile plants with good segregation (1:1) of male-sterile phenotype in progeny/Nr of analyzed male-sterile plants
[5]Number of selected calli was significantly less when compared to calli of transformation experiments containing P35S-barstar
[6]Cotransformation experiments using pDE110 in combination with plasmids not comprising cytotoxic genes.

TABLE 3

| | T0[1] | T1[2] | | T2 Progeny Analysis[3] |
|---|---|---|---|---|
| | | F/S at 50% Flowering | F/S at 100% Flowering | |
| pTHW107 | 20/22 | 72%/28% | 54%/46% | 2/7 |
| pTCO113 | 27/31 | 62%/38% | 54%/46% | 12/14 |

[1]T0: Number of transformed plants that were male-sterile/number of Bastatolerant plants regenerated after transformation.
[2]T1: percentage of T1 plants with male-fertile flowers (F)/percentage of T1 plants with male-sterile flowers (S) at a time that 50%, respectively 100%, of the T1 plants started to flower. Data from different lines (18 pTHW107 and 17 pTCO113 lines respectively) were pooled.
[3]T2: Number of T1 lines that have a normal 1:1 segregation of the male-sterility gene/total numbers of T1 lines that were examined in the field.

We claim:

1. A plant having in the nuclear genome of its cells a foreign DNA comprising:

a male-sterility gene comprising:
  a male sterility DNA encoding a ribonuclease; and
  a sterility promoter directing expression of said male-sterility DNA selectively in specific stamen cells of said plant, said male-sterility DNA being in the same transcriptional unit as, and under the control of, said sterility promoter; and a coregulating gene comprising:
  a coregulating DNA encoding a ribonuclease inhibitor which is capable of neutralizing, blocking, preventing or inhibiting the activity of said ribonuclease; and
  a coregulating promoter which is selected from the group consisting of: a promoter directing expression of said coregulating DNA in non-stamen cells of said plant, while directing low-level expression in said specific stamen cells; and a promoter comprising a minimal promoter element;

wherein said coregulating DNA is in the same transcriptional unit as, and under the control of, said coregulating promoter;

wherein said coregulating DNA is in a transcriptional unit which is different from the transcriptional unit of said sterility DNA and wherein said plant is male-sterile.

2. The plant of claim 1, in which said male-sterility gene and said coregulating gene are adjacent to one another.

3. The plant of claim 1, wherein said sterility DNA encodes barnase or a variant thereof.

4. The plant of claim 1, wherein said coregulating DNA encodes barstar or a variant thereof.

5. The plant of claim 1, wherein said sterility DNA encodes barnase or a variant thereof and said coregulating DNA encodes barstar, or a variant thereof.

6. The plant of claim 1, wherein said specific stamen cells are anther cells.

7. The plant of claim 1, wherein said specific stamen cells are tapetum cells.

8. The plant of claim 1, wherein said sterility promoter is PTA29.

9. The plant of claim 1, in which said sterility promoter is selected from the group consisting of PCA55, PE1, PT72 and PT42.

10. The plant of claim 1, wherein said coregulating promoter directs expression of said coregulating DNA in non-stamen cells and directs low-level expression in said specific stamen cells.

11. The plant of claim 1, wherein said coregulating promoter directs expression of said coregulating DNA in at least a majority of non-stamen cells.

12. The plant of claim 1, wherein said coregulating promoter directs expression of said coregulating DNA in non-stamen cells; but does not direct expression in said specific stamen cells.

13. The plant of claim 1, wherein said coregulating promoter comprises a minimal promoter element which is from a promoter normally expressed in plant cells.

14. The plant of claim 1, wherein said coregulating promoter is a CaMV 35S promoter.

15. The plant of claim 1, wherein said coregulating promoter is a Pnos promoter.

16. The plant of claim 1, wherein said coregulating DNA is under the control of enhancer elements in the nuclear genome of said plant.

17. The plant of claim 1, which is a dicotyledonous plant.

18. The plant of claim 17, which is a Brassica plant.

19. The plant of claim 1, which is a monocotyledonous plant.

20. The plant of claim 19, which is corn or rice.

21. A cell of a plant according to claim 1.

22. A process to obtain a male-sterile plant, which process comprises the steps of:

(1) transforming the nuclear genome of plant cells with a foreign DNA comprising:

a) a male-sterility gene comprising:

a male-sterility DNA encoding a ribonuclease; and, a sterility promoter capable of directing expression of the male-sterility DNA selectively in specific stamen cells of said plant; said male-sterility DNA being in the same transcriptional unit as, and under the control of, said sterility promoter, and b) a coregulating gene comprising a coregulating DNA encoding a ribonuclease inhibitor, which is capable of neutralizing, blocking, preventing or inhibiting the activity of a ribonuclease; wherein said coregulating DNA is not under the control of a promoter directing expression in plant cells whereby said coregulating DNA is capable of being placed under the control of enhancer elements in the nuclear genome of said plant after integration of said foreign DNA in said plant genome; or is under the control of a coregulating promoter which is selected from the group consisting of: a promoter capable of directing expression of said coregulating DNA in non-stamen cells while directing low-level expression in said specific stamen calls and a promoter comprising a minimal promoter element;

(2) regenerating a plant from said transformed plant cells; and (3) selecting regenerated plants that are male-sterile.

23. The process of claim 22, wherein said sterility DNA encodes barnase.

24. The process of claim 22, wherein said coregulating DNA encodes barstar or a variant thereof.

25. The process of claim 22, wherein said sterility DNA encodes barnase or a variant thereof and said coregulating DNA encodes barstar or a variant thereof.

26. The process of claim 22, wherein said specific stamen cells are anther cells.

27. The process of claim 22, wherein said specific stamen cells are tapetum cells.

28. The process of claim 22, wherein said sterility promoter is PTA29.

29. The process of claim 22, wherein said sterility promoter is selected from the group consisting of PCA55, PE1, PT72 and PT42.

30. The process of claim 22, wherein said coregulating promoter directs expression of said coregulating DNA in at least a majority of non-stamen cells.

31. The process of claim 22, wherein said coregulating promoter directs expression of said coregulating DNA in non-stamen cells but does not direct expression in said specific stamen cells.

32. The process of claim 22, wherein said coregulating promoter comprises a minimal promoter element which is from a promoter normally expressed in plant cells.

33. The process of claim 22, wherein said coregulating promoter is a CaMV 35S promoter.

34. The process of claim 22, wherein said coregulating promoter is a Pnos promoter.

35. The process of claim 22, wherein said coregulating DNA is under the control of enhancer elements in the nuclear genome of said plant.

36. The process of claim 22, wherein said male-sterile plant is a dicotyledonous plant.

37. The process of claim 36, wherein said dicotyledonous plant is a Brassica plant.

38. The process of claim 22, wherein said male-sterile plant is a monocotyledonous plant.

39. The process of claim 38, wherein said monocotyledonous plant is corn or rice.

40. A plant obtained by the process according to claim 22.

* * * * *

SEQUENCE LISTING

<160> NUMBER OF SEQ ID NOS: 4

<210> SEQ ID NO 1
<211> LENGTH: 6548
<212> TYPE: DNA
<213> ORGANISM: Artificial Sequence
<220> FEATURE:
<223> OTHER INFORMATION: Description of Artificial Sequence: plasmid pTS174
<220> FEATURE:
<221> NAME/KEY: misc_feature
<222> LOCATION: (1)..(2003)
<223> OTHER INFORMATION: pUC19 derived vector sequences (vector)
<220> FEATURE:
<221> NAME/KEY: misc_feature
<222> LOCATION: Complement((2019)..(2283))
<223> OTHER INFORMATION: 3' nos: region containing polyadenylation signal of nopaline synthase gene of Agrobacterium
<220> FEATURE:
<221> NAME/KEY: misc_feature
<222> LOCATION: Complement((2284)..(2624))
<223> OTHER INFORMATION: region coding for barnase of Bacillus amyloliquefaciens
<220> FEATURE:
<221> NAME/KEY: misc_feature
<222> LOCATION: Complement((2625)..(4313))
<223> OTHER INFORMATION: promoter of the stamen-specific E1 gene of rice (PE1)
<220> FEATURE:
<221> NAME/KEY: misc_feature
<222> LOCATION: (4336)..(5710)
<223> OTHER INFORMATION: 35S promoter of Cauliflower Mosaic Virus (P35S)
<220> FEATURE:
<221> NAME/KEY: misc_feature
<222> LOCATION: (5711)..(6262)
<223> OTHER INFORMATION: region coding for phosphinothricin acetyl transferase (bar)
<220> FEATURE:
<221> NAME/KEY: misc_feature
<222> LOCATION: (6263)..(6496)
<223> OTHER INFORMATION: region containing polyadenylation signal fo gene 7 of Agrobacterium T-DNA (3'g7)

<400> SEQUENCE: 1

| | | | | | |
|---|---|---|---|---|---|
| aattcaagct | tgacgtcagg | tggcactttt | cggggaaatg | tgcgcggaac | ccctatttgt | 60 |
| ttatttttct | aaatacattc | aaatatgtat | ccgctcatga | gacaataacc | ctgataaatg | 120 |
| cttcaataat | attgaaaaag | gaagagtatg | agtattcaac | atttccgtgt | cgcccttatt | 180 |
| ccctttttg | cggcattttg | ccttcctgtt | tttgctcacc | cagaaacgct | ggtgaaagta | 240 |
| aaagatgctg | aagatcagtt | gggtgcacga | gtgggttaca | tcgaactgga | tctcaacagc | 300 |
| ggtaagatcc | ttgagagttt | tcgccccgaa | gaacgttttc | caatgatgag | cacttttaaa | 360 |
| gttctgctat | gtggcgcggt | attatcccgt | attgacgccg | ggcaagagca | actcggtcgc | 420 |
| cgcatacact | attctcagaa | tgacttggtt | gagtactcac | cagtcacaga | aaagcatctt | 480 |
| acggatggca | tgacagtaag | agaattatgc | agtgctgcca | taaccatgag | tgataacact | 540 |
| gcggccaact | tacttctgac | aacgatcgga | ggaccgaagg | agctaaccgc | ttttttgcac | 600 |
| aacatggggg | atcatgtaac | tcgccttgat | cgttgggaac | cggagctgaa | tgaagccata | 660 |
| ccaaacgacg | agcgtgacac | cacgatgcct | gtagcaatgg | caacaacgtt | gcgcaaacta | 720 |
| ttaactggcg | aactacttac | tctagcttcc | cggcaacaat | taatagactg | gatggaggcg | 780 |
| gataaagttg | caggaccact | tctgcgctcg | gcccttccgg | ctggctggtt | tattgctgat | 840 |
| aaatctggag | ccggtgagcg | tgggtctcgc | ggtatcattg | cagcactggg | gccagatggt | 900 |
| aagccctccc | gtatcgtagt | tatctacacg | acggggagtc | aggcaactat | ggatgaacga | 960 |

```
aatagacaga tcgctgagat aggtgcctca ctgattaagc attggtaact gtcacaccaa   1020
gtttactcat atatacttta gattgattta aaacttcatt tttaatttaa aaggatctag   1080
gtgaagatcc ttttttggctc gagtctcatg accaaaatcc cttaacgtga gttttcgttc   1140
cactgagcgt cagaccccgt agaaaagatc aaaggatctt cttgagatcc ttttttttctg   1200 cgcgtaatct gctgcttgca acaaaaaaaa ccaccgctac cagcggtggt ttgtttgccg   1260
gatcaagagc taccaactct ttttccgaag gtaactggct tcagcagagc gcagatacca   1320
aatactgtcc ttctagtgta gccgtagtta ggccaccact tcaagaactc tgtagcaccg   1380
cctacatacc tcgctctgct aatcctgtta ccagtggctg ctgccagtgg cgataagtcg   1440
tgtcttaccg ggttggactc aagacgatag ttaccggata aggcgcagcg gtcgggctga   1500
acggggggtt cgtgcacaca gcccagcttg gagcgaacga cctacaccga actgagatac   1560
ctacagcgtg agcattgaga aagcgccacg cttcccgaag ggagaaaggc ggacaggtat   1620
ccggtaagcg gcagggtcgg aacaggagag cgcacgaggg agcttccagg gggaaacgcc   1680
tggtatcttt atagtcctgt cgggtttcgc cacctctgac ttgagcgtcg attttttgtga   1740 tgctcgtcag gggggcggag cctatggaaa aacgccagca acgcggcctt tttacggttc   1800 ctggccttt gctggccttt tgctcacatg ttctttcctg cgttatcccc tgattctgtg   1860
gataaccgta ttaccgcctt tgagtgagct gataccgctc gccgcagccg aacgaccgag   1920
cgcagcgagt cagtgagcga ggaagcggaa gagcgcccaa tacgcaaacc gcctctcccc   1980
gcgcgttggc ctgatcagaa ttcatatgca cgtgttcccg atctagtaac atagatgaca   2040
ccgcgcgcga taatttatcc tagtttgcgc gctatatttt gttttctatc gcgtattaaa   2100
tgtataattg cgggactcta atcataaaaa cccatctcat aaataacgtc atgcattaca   2160
tgttaattat tacatgctta acgtaattca acagaaatta tatgataatc atcgcaagac   2220
cggcaacagg attcaatctt aagaaacttt attgccaaat gtttgaacga tctgcttcgg   2280
aggttacctt atctgatttt tgtaaaggtc tgataatggt ccgttgtttt gtaaatcagc   2340
cagtcgcttg agtaaagaat ccggtctgaa tttctgaagc ctgatgtata gttaatatcc   2400
gcttcacgcc atgttcgtcc gcttttgccc gggagtttgc cttccctgtt tgagaagatg   2460
tctccgccga tgcttttccc cggagcgacg tctgcaaggt tccctttga tgccacccag   2520 ccgagggctt gtgcttctga ttttgtaatg taattatcag gtagcttatg atatgtctga   2580
agataatccg caaccccgtc aaacgtgttg ataaccggta ccatcgagac ggcttgatgg   2640
atctcttgct ggacaccggg atgctaggat gggttatcgt ggccggcgtg cgtgtgtggc   2700
ttttgtaggc gccggcgacg gcgggggcaa tgtggcaggt gagtcacggt gcaagcgtgc   2760
gcaagtgact gcaacaacca aggacggtca tggcgaaagc acctcacgcg tccaccgtct   2820
acaggatgta gcagtagcac ggtgaaagaa gtgttgtccc gtccattagg tgcattctca   2880
ccgttggcca gaacaggacc gttcaacagt taggttgagt gtaggacttt tacgtggtta   2940
atgtatggca aatagtagta aattttgccc ccattggtct ggctgagata gaacatattc   3000
tggaaagcct ctagcatatc ttttttgaca gctaaacttt gcttcttgcc ttcttggtct   3060
agcaatgacg ttgcccatgt cgtggcaaac atctggtaag gtaactgtat tcgtttgttc   3120
ccttcaacgg ctcaatcccc acaggccaag ctatcctttc cttggcagta taggctcctt   3180
gagagattat actaccattt ttaagtgctt ataaagacga tgctctctaa ccagatcgat   3240
cagaaacaca aagttttagc agcgtaatat cccacacaca tacacacacg aagctatgcc   3300
```

-continued

| | |
|---|---|
| tcctcattttt ccgagagatt ctgacagtga ccagaatgtc agaatgccat ttcatgggca | 3360 |
| caagtcgatc cacaagcttc ttggtggagg tcaaggtgtg ctattattat tcgctttcta | 3420 |
| ggaaattatt cagaattagt gccttttatc ataacttctc tctgagccga tgtggttttg | 3480 |
| gatttcattg ttgggagcta tgcagttgcg gatattctgc tgtggaagaa caggaactta | 3540 |
| tctgcggggg tccttgctgg ggcaacattg atatggttcc tgttcgatgt agtagaatac | 3600 |
| aatataattc cgctcctttg ccagattgcc attcttgcca tgcttgtgat cttcatttgg | 3660 |
| tcaaatgccg caccactctt ggacaggtat tagctttatt tcctgtggag atggtagaaa | 3720 |
| actcagctta cagaaatggc atttcacgta gtataacgca agacattagg tactaaaact | 3780 |
| caactaactg tttccgaatt tcagggcccc tccaaggatc ccagaaatca tcatctctga | 3840 |
| acatgccttc agagaaatgg cattgaccgt ccattacaaa ctaacgtaca ctgtatctgt | 3900 |
| tctttacgac attgcatgtg gaaggatct gaagagattt ctcctggtac ataataatct | 3960 |
| actcctttgc tacgttaata agagatgtaa aaacatgcaa cagttccagt gccaacattg | 4020 |
| tccaaggatt gtgcaattct ttctggagcg ctaaaattga ccagattaga cgcatcagaa | 4080 |
| tattgaattg cagagttagc caataatcct cataatgtta atgtgctatt gttgttcact | 4140 |
| actcaatata gttctggact aacaatcaga ttgtttatga tattaaggtg gttggatctc | 4200 |
| tattggtatt gtcggcgatt ggaagttctt gcagcttgac aagtctacta tatattggta | 4260 |
| ggtattccag ataaatatta aattttaata aaacaatcac acagaaggat ctgcggccgc | 4320 |
| tagcctaggc ccgggcccac aaaaatctga gcttaacagc acagttgctc ctctcagagc | 4380 |
| agaatcgggt attcaacacc ctcatatcaa ctactacgtt gtgtataacg gtccacatgc | 4440 |
| cggtatatac gatgactggg gttgtacaaa ggcggcaaca aacggcgttc ccggagttgc | 4500 |
| acacaagaaa tttgccacta ttacagaggc aagagcagca gctgacgcgt acacaacaag | 4560 |
| tcagcaaaca gacaggttga acttcatccc caaggagaa gctcaactca gcccaagag | 4620 |
| ctttgctaag gccctaacaa gcccaccaaa gcaaaaagcc cactggctca cgctaggaac | 4680 |
| caaaaggccc agcagtgatc cagccccaaa agagatctcc tttgccccgg agattacaat | 4740 |
| ggacgatttc ctctatcttt acgatctagg aaggaagttc gaaggtgaag gtgacgacac | 4800 |
| tatgttcacc actgataatg agaaggttag cctcttcaat ttcagaaaga atgctgaccc | 4860 |
| acagatggtt agagaggcct acgcagcagg tctcatcaag acgatctacc cgagtaacaa | 4920 |
| tctccaggag atcaaatacc ttcccaagaa ggttaaagat gcagtcaaaa gattcaggac | 4980 |
| taattgcatc aagaacacag agaaagacat atttctcaag atcagaagta ctattccagt | 5040 |
| atggacgatt caaggcttgc ttcataaacc aaggcaagta atagagattg gagtctctaa | 5100 |
| aaaggtagtt cctactgaat ctaaggccat gcatggagtc taagattcaa atcgaggatc | 5160 |
| taacagaact cgccgtgaag actggcgaac agttcataca gagtctttta cgactcaatg | 5220 |
| acaagaagaa aatcttcgtc aacatggtgg agcacgacac tctggtctac tccaaaaatg | 5280 |
| tcaaagatac agtctcagaa gaccaaaggg ctattgagac ttttcaacaa aggataattt | 5340 |
| cgggaaacct cctcggattc cattgcccag ctatctgtca cttcatcgaa aggacagtag | 5400 |
| aaaaggaagg tggctcctac aaatgccatc attgcgataa aggaaaggct atcattcaag | 5460 |
| atgcctctgc cgacagtggt cccaaagatg gacccccacc cacgaggagc atcgtggaaa | 5520 |
| aagaagacgt tccaaccacg tcttcaaagc aagtggattg atgtgacatc tccactgacg | 5580 |
| taagggatga cgcacaatcc cactatcctt cgcaagaccc ttcctctata taaggaagtt | 5640 |
| catttcattt ggagaggaca cgctgaaatc accagtctct ctctataaat ctatctctct | 5700 |

-continued

```
ctctataacc atggacccag aacgacgccc ggccgacatc cgccgtgcca cccaggcgga    5760
catgccggcg gtctgcacca tcgtcaacca ctacatcgag acaagcacgg tcaacttccg    5820
taccgagccg caggaaccgc aggagtggac ggacgacctc gtccgtctgc gggagcgcta    5880
tccctggctc gtcgccgagg tggacggcga ggtcgccggc atcgcctacg cgggcccctg    5940
gaaggcacgc aacgcctacg actggacggc cgagtcgacc gtgtacgtct cccccgcca    6000 ccagcggacg ggactgggct ccacgctcta cacccacctg ctgaagtccc tggaggcaca    6060
gggcttcaag agcgtggtcg ctgtcatcgg gctgcccaac gacccgagcg tgcgcatgca    6120
cgaggcgctc ggatatgccc cccgcggcat gctgcgggcg gccggcttca agcacgggaa    6180
ctggcatgac gtgggtttct ggcagctgga cttcagcctg ccggtaccgc ccgtccggt    6240 cctgcccgtc accgagatct gagatcacgc gttctaggat cccccgatga gctaagctag    6300
ctatatcatc aatttatgta ttacacataa tatcgcactc agtctttcat ctacggcaat    6360
gtaccagctg atataatcag ttattgaaat atttctgaat ttaaacttgc atcaataaat    6420
ttatgttttt gcttggacta taatacctga cttgttattt tatcaataaa tatttaaact    6480
atatttcttt caagatggga attaacatct acaaattgcc ttttcttatc gaccatgtac    6540
gtatcgcg                                                             6548
```

<210> SEQ ID NO 2
<211> LENGTH: 1303
<212> TYPE: DNA
<213> ORGANISM: Artificial Sequence
<220> FEATURE:
<223> OTHER INFORMATION: Description of Artificial Sequence:
      HindIII-EcoRI fragment of pTS88
<220> FEATURE:
<221> NAME/KEY: misc_feature
<222> LOCATION: (1)..(35)
<223> OTHER INFORMATION: polylinker of pGEM2 (pGEM2)
<220> FEATURE:
<221> NAME/KEY: misc_feature
<222> LOCATION: (36)..(694)
<223> OTHER INFORMATION: 35S promoter of Cauliflower Mosaic Virus strain
      CM1841 (P35S)
<220> FEATURE:
<221> NAME/KEY: misc_feature
<222> LOCATION: (695)..(967)
<223> OTHER INFORMATION: region coding for barstar of Bacillus
      amyloliquefaciens
<220> FEATURE:
<221> NAME/KEY: misc_feature
<222> LOCATION: (968)..(1287)
<223> OTHER INFORMATION: region containing polyadenylation signal of
      gene 7 of Agrobacterium T-DNA (3'g7)
<220> FEATURE:
<221> NAME/KEY: misc_feature
<222> LOCATION: (1288)..(1303)
<223> OTHER INFORMATION: polylinker of pGEM2

<400> SEQUENCE: 2

```
aagcttgggc tgcaggtcga ctctagagga tccccactat tccagtatgg acgattcaag     60
gcttgcttca taaccaagg caagtaatag agattggagt ctctaagaaa gtagttccta    120
ctgaatcaaa ggccatggag tcaaaaattc agatcgagga tctaacagaa ctcgccgtga    180
agactggcga acagttcata cagagtcttt tacgactcaa tgacaagaag aaaatcttcg    240
tcaacatggt ggagcacgac actctcgtct actccaagaa tatcaaagat acagtctcag    300
aagaccaaag ggctattgag acttttcaac aaagggtaat atcgggaaac ctcctcggat    360
tccattgccc agctatctgt cacttcatca aaaggacagt agaaaaggaa ggtggcacct    420
```

```
acaaatgcca tcattgcgat aaaggaaagg ctatcgttca agatgcctct gccgacagtg      480
gtcccaaaga tggaccccca cccacgagga gcatcgtgga aaaagaagac gttccaacca      540
cgtcttcaaa gcaagtggat tgatgtgata tctccactga cgtaagggat gacgcacaat      600
cccactatcc ttcgcaagac ccttcctcta tataaggaag ttcatttcat ttggagagga      660
cacgctgaaa tcaccagtct ctctctacaa atcgatgaaa aaagcagtca ttaacgggga      720
acaaatcaga agtatcagcg acctccacca gacattgaaa aaggagcttg cccttccgga      780
atactacggt gaaaacctgg acgctttatg ggattgtctg accggatggg tggagtaccc      840
gctcgttttg gaatggaggc agtttgaaca aagcaagcag ctgactgaaa atggcgccga      900
gagtgtgctt caggttttcc gtgaagcgaa agcggaaggc tgcgacatca ccatcatact      960
ttcttaatac gatcaatggg agatgaacaa tatggaaaca caaacccgca agcttggtct     1020
agaggatccc ccgatgagct aagctagcta tatcatcaat ttatgtatta cacataaatt     1080
cgcactcagt ctttcatcta cggcaatgta ccagctgata taatcagtta ttgaaatatt     1140
tctgaattta aacttgcatc aataaattta tgttttgct tggactataa tacctgactt      1200
gttattttat caataaatat ttaaactata tttctttcaa gatgggaatt aacatctaca     1260
aattgccttt tcttatcgac catgtacggg cgagctcgaa ttc                       1303
```

<210> SEQ ID NO 3
<211> LENGTH: 3658
<212> TYPE: DNA
<213> ORGANISM: Artificial Sequence
<220> FEATURE:
<223> OTHER INFORMATION: Description of Artificial Sequence:
      EcoRI-HindIII fragment of pVE136
<220> FEATURE:
<221> NAME/KEY: misc_feature
<222> LOCATION: (1)..(26)
<223> OTHER INFORMATION: polylinker of pUC19
<220> FEATURE:
<221> NAME/KEY: misc_feature
<222> LOCATION: Complement((28)..(403))
<223> OTHER INFORMATION: region containing polyadenylation signal of
      nopaline synthase gene of Agrobacterium T-DNA
      (3'nos)
<220> FEATURE:
<221> NAME/KEY: misc_feature
<222> LOCATION: Complement((404)..(739))
<223> OTHER INFORMATION: region coding for barnase of Bacillus
      amyloliquefaciens
<220> FEATURE:
<221> NAME/KEY: misc_feature
<222> LOCATION: Complement((740)..(1918))
<223> OTHER INFORMATION: promoter of CA55 gene of Zea mays (PCA55)
<220> FEATURE:
<221> NAME/KEY: misc_feature
<222> LOCATION: (1956)..(2788)
<223> OTHER INFORMATION: 35S promoter of Cauliflower Mosaic Virus (35S)
<220> FEATURE:
<221> NAME/KEY: misc_feature
<222> LOCATION: (2789)..(3340)
<223> OTHER INFORMATION: region coding for phosphinothricin acetyl
      transferase (bar)
<220> FEATURE:
<221> NAME/KEY: misc_feature
<222> LOCATION: (3341)..(3623)
<223> OTHER INFORMATION: region containing polyadenylation signal of
      nopaline synthase gene of Agrobacterium T-DNA
      (3'nos)
<220> FEATURE:
<221> NAME/KEY: misc_feature
<222> LOCATION: (3624)..(3658)
<223> OTHER INFORMATION: polylinker of pUC19

<400> SEQUENCE: 3

-continued

```
gaattcgagc tcggtacccg gggatcttcc cgatctagta acatagatga caccgcgcgc      60
gataatttat cctagtttgc gcgctatatt ttgttttcta tcgcgtatta aatgtataat     120
tgcgggactc taatcataaa aacccatctc ataaataacg tcatgcatta catgttaatt     180
attacatgct taacgtaatt caacagaaat tatatgataa tcatcgcaag accggcaaca     240
ggattcaatc ttaagaaact ttattgccaa atgtttgaac gatctgcttc ggatcctcta     300
gagccggaaa gtgaaattga ccgatcagag tttgaagaaa aatttattac acactttatg     360
taaagctgaa aaaacggcc tccgcaggaa gccgtttttt tcgttatctg attttgtaa       420 aggtctgata atggtccgtt gttttgtaaa tcagccagtc gcttgagtaa agaatccggt     480
ctgaatttct gaagcctgat gtatagttaa tatccgcttc acgccatgtt cgtccgcttt     540
tgcccgggag tttgccttcc ctgtttgaga agatgtctcc gccgatgctt ttccccggag     600
cgacgtctgc aaggttccct tttgatgcca cccagccgag ggcttgtgct tctgattttg     660
taatgtaatt atcaggtagc ttatgatatg tctgaagata atccgcaacc ccgtcaaacg     720
tgttgataac cggtaccatg gctgcagcta gttagctcga tgtatcttct gtatatgcag     780
tgcagcttct gcgttttggc tgctttgagc tgtgaaatct cgctttccag tccctgcgtg     840
ttttatagtg ctgtacgttc gtgatcgtga gcaaacaggg cgtgcctcaa ctactggttt     900
ggttgggtga caggcgccaa ctacgtgctc gtaaccgatc gagtgagcgt aatgcaacat     960 ttttcttct tctctcgcat tggtttcatc cagccaggag acccgaatcg aattgaaatc     1020
acaaatctga ggtacagtat ttttacagta ccgttcgttc gaaggtcttc gacaggtcaa     1080
ggtaacaaaa tcagttttaa attgttgttt cagatcaaag aaaattgaga tgatctgaag     1140
gacttggacc ttcgtccaat gaaacacttg gactaattag aggtgaattg aaagcaagca     1200
gatgcaaccg aaggtggtga agtggagtt tcagcattga cgacgaaaac cttcgaacgg     1260
tataaaaaag aagccgcaat taaacgaaga tttgccaaaa agatgcatca accaagggaa     1320
gacgtgcata catgtttgat gaaaactcgt aaaaactgaa gtacgattcc ccattcccct     1380 cctttctcg tttcttttaa ctgaagcaaa gaatttgtat gtattccctc cattccatat      1440
tctaggaggt tttggctttt catccctcc tccatttcaa attatttgtc atacattgaa      1500
gatatacacc attctaattt atactaaatt acagctttta gatacatata ttttattata     1560
cacttagata cgtattatat aaaacaccta atttaaaata aaaaattata taaaaagtgt     1620
atctaaaaaa tcaaaatacg acataatttg aaacggaggg gtactactta tgcaaaccaa     1680
tcgtggtaac cctaaacccct atatgaatga ggccatgatt gtaatgcacc gtctgattaa    1740
ccaagatatc aatggtcaaa gatatacatg atacatccaa gtcacagcga aggcaaatgt    1800
gacaacagtt tttttacca gagggacaag ggagaatatc tattcagatg tcaagttccc     1860
gtatcacact gccaggtcct tactccagac catcttccgg ctctattgat gcataccagg    1920
aattgatcta gagtcgacct gcaggcatgc aagctcctac gcagcaggtc tcatcaagac    1980
gatctacccg agtaacaatc tccaggagat caaatacctt cccaagaagg ttaaagatgc    2040
agtcaaaaga ttcaggacta attgcatcaa gaacacagag aaagacatat ttctcaagat    2100
cagaagtact attccagtat ggacgattca aggcttgctt cataaaccaa ggcaagtaat    2160
agagattgga gtctctaaaa aggtagttcc tactgaatct aaggccatgc atggagtcta    2220
agattcaaat cgaggatcta acagaactcg ccgtgaagac tggcgaacag ttcatacaga    2280 gtctttacg actcaatgac aagaagaaaa tcttcgtcaa catggtggag cacgacactc     2340
tggtctactc caaaaatgtc aaagatacag tctcagaaga ccaaagggct attcagactt    2400
```

```
ttcaacaaag gataatttcg ggaaacctcc tcggattcca ttgcccagct atctgtcact    2460
tcatcgaaag gacagtagaa aaggaaggtg gctcctacaa atgccatcat tgcgataaag    2520
gaaaggctat cattcaagat gcctctgccg acagtggtcc caaagatgga cccccaccca    2580
cgaggagcat cgtggaaaaa gaagacgttc caaccacgtc ttcaaagcaa gtggattgat    2640
gtgacatctc cactgacgta agggatgacg cacaatccca ctatccttcg caagacccttr   2700 cctctatata aggaagttca tttcatttgg agaggacacg ctgaaatcac cagtctctct    2760
ctataaatct atctctctct ctataaccat ggacccagaa cgacgcccgg ccgacatccg    2820
ccgtgccacc gaggcggaca tgccggcggt ctgcaccatc gtcaaccact acatcgagac    2880
aagcacggtc aacttccgta ccgagccgca ggaaccgcag gagtggacgg acgacctcgt    2940
ccgtctgcgg gagcgctatc cctggctcgt cgccgaggtg gacggcgagg tcgccggcat    3000
cgcctacgcg ggcccctgga aggcacgcaa cgcctacgac tggacggccg agtcgaccgt    3060
gtacgtctcc ccccgccacc agcggacggg actgggctcc acgctctaca cccacctgct    3120
gaagtccctg gaggcacagg gcttcaagag cgtggtcgct gtcatcgggc tgcccaacga    3180
cccgagcgtg cgcatgcacg aggcgctcgg atatgccccc cgcggcatgc tgcgggcggc    3240
cggcttcaag cacgggaact ggcatgacgt gggtttctgg cagctggact tcagcctgcc    3300
ggtaccgccc cgtccggtcc tgcccgtcac cgagatctga tctcacgcgt ctaggatccg    3360
aagcagatcg ttcaaacatt tggcaataaa gtttcttaag attgaatcct gttgccggtc    3420
ttgcgatgat tatcatataa tttctgttga attacgttaa gcatgtaata attaacatgt    3480
aatgcatgac gttatttatg agatgggttt ttatgattag agtcccgcaa ttatacattt    3540
aatacgcgat agaaaacaaa atatagcgcg caaactagga taaattatcg cgcgcggtgt    3600
catctatgtt actagatcgg gaagatcctc tagagtcgac ctgcaggcat gcaagctt     3658

<210> SEQ ID NO 4
<211> LENGTH: 5864
<212> TYPE: DNA
<213> ORGANISM: Artificial Sequence
<220> FEATURE:
<223> OTHER INFORMATION: Description of Artificial Sequence: T-DNA of
      plasmid pTCO113
<220> FEATURE:
<221> NAME/KEY: misc_feature
<222> LOCATION: Complement((1)..(25))
<223> OTHER INFORMATION: right border of Agrobacterium T-DNA (RB)
<220> FEATURE:
<221> NAME/KEY: misc_feature
<222> LOCATION: Complement((98)..(330))
<223> OTHER INFORMATION: region containing polyadenylation signal of
      gene 7 of Agrobacterium T-DNA (3'g7)
<220> FEATURE:
<221> NAME/KEY: misc_feature
<222> LOCATION: Complement((331)..(882))
<223> OTHER INFORMATION: region coding for phosphinothricin acetyl
      transferase (bar)
<220> FEATURE:
<221> NAME/KEY: misc_feature
<222> LOCATION: Complement((883)..(2608))
<223> OTHER INFORMATION: promoter of small subunit gene of Rubisco of
      Arabidopsis (Pssu)
<220> FEATURE:
<221> NAME/KEY: misc_feature
<222> LOCATION: Complement((2659)..(3031))
<223> OTHER INFORMATION: region containing polyadenylation signal of
      nopaline synthase gene of Agrobacterium T-DNA
      (3'nos)
<220> FEATURE:
<221> NAME/KEY: misc_feature
<222> LOCATION: Complement((3032)..(3367))
```

```
<223> OTHER INFORMATION: region coding for barnase of Bacillus
      amyloliquefaciens
<220> FEATURE:
<221> NAME/KEY: misc_feature
<222> LOCATION: Complement((3368)..(4877))
<223> OTHER INFORMATION: promoter of stamen-specific TA29 gene of
      Nicotiana tabacum (PTA29)
<220> FEATURE:
<221> NAME/KEY: misc_feature
<222> LOCATION: (4924)..(5216)
<223> OTHER INFORMATION: promoter of nopaline synthase gene of
      Agrobacterium T-DNA (Pnos)
<220> FEATURE:
<221> NAME/KEY: misc_feature
<222> LOCATION: (5217)..(5489)
<223> OTHER INFORMATION: region coding for barstar of Bacillus
      amyloliquefaciens
<220> FEATURE:
<221> NAME/KEY: misc_feature
<222> LOCATION: (5490)..(5765)
<223> OTHER INFORMATION: region containing polyadenylation signal of
      gene 7 of Agrobacterium T-DNA (3'g7)
<220> FEATURE:
<221> NAME/KEY: misc_feature
<222> LOCATION: Complement((5840)..(5864))
<223> OTHER INFORMATION: left border of Agrobacterium T-DNA

<400> SEQUENCE: 4
aattacaacg gtatatatcc tgccagtact cggccgtcga actcggccgt cgagtacatg      60
gtcgataaga aaggcaatt tgtagatgtt aattcccatc ttgaaagaaa tatagtttaa     120
atatttattg ataaaataac aagtcaggta ttatagtcca agcaaakaca taaatttatt    180
gatgcaagtt taaattcaga aatatttcaa taactgatta tatcagctgg tacattgccg    240
tagatgaaag actgagtgcg atattatgtg taatacataa attgatgata tagctagctt    300
agctcatcgg gggatcctag acgcgtgaga tcagatctcg gtgacgggca ggaccggacg    360
gggcggtacc ggcaggctga agtccagctg ccagaaaccc acgtcatgcc agttcccgtg    420
cttgaagccg gccgcccgca gcatgccgcg gggggcatat ccgagcgcct cgtgcatgcg    480
cacgctcggg tcgttgggca gcccgatgac agcgaccacg ctcttgaagc cctgtgcctc    540
cagggacttc agcaggtggg tgtagagcgt ggagcccagt cccgtccgct ggtggcgggg    600
ggagacgtac acggtcgact cggccgtcca gtcgtaggcg ttgcgtgcct tccaggggcc    660
cgcgtaggcg atgccggcga cctcgccgtc cacctcggcg acgagccagg gatagcgctc    720
ccgcagacgg acgaggtcgt ccgtccactc ctgcggttcc tgcggctcgg tacgaagtt    780 gaccgtgctt gtctcgatgt agtggttgac gatggtgcag accgccggca tgtccgcctc    840
ggtggcacgg cggatgtcgg ccgggcgtcg ttctgggtcc attgttcttc tttactcttt    900
gtgtgactga ggtttggtct agtgctttgg tcatctatat ataatgataa caacaatgag    960
aacaagcttt ggagtgatcg gagggtctag gatacatgag attcaagtgg actaggatct   1020
acaccgttta atttgagtg tggatatgtg tgaggttaat tttacttggt aacgccaca    1080 aaggcctaag gagaggtgtt gagaccctta tcggcttgaa ccgctggaat aatgccacgt   1140
ggaagataat tccatgaatc ttatcgttat ctatgagtga aattgtgtga tggtggagtg   1200
gtgcttgctc atttacttg cctggtggac ttggccctt ccttatgggg aatttatatt   1260
ttacttacta tagagctttc ataccttttt tttaccttgg atttagttaa tatataatgg   1320
tatgattcat gaataaaaat gggaaatttt tgaatttgta ctgctaaatg cataagatta   1380
ggtgaaactg tggaatatat attttttttca tttaaaagca aaatttgcct tttactagaa   1440
ttataaatat agaaaaatat ataacattca aataaaaatg aaaataagaa ctttcaaaaa   1500
```

-continued

```
acagaactat gtttaatgtg taaagattag tcgcacatca agtcatctgt tacaatatgt      1560
tacaacaagt cataagccca acaaagttag cacgtctaaa taaactaaag agtccacgaa      1620
aatattacaa atcataagcc caacaaagtt attgatcaaa aaaaaaaaac gcccaacaaa      1680
gctaaacaaa gtccaaaaaa aacttctcaa gtctccatct tcctttatga acattgaaaa      1740
ctatacacaa aacaagtcag ataaatctct ttctgggcct gtcttcccaa cctcctacat      1800
cacttcccta tcggattgaa tgttttactt gtaccttttc cgttgcaatg atattgatag      1860
tatgtttgtg aaaactaata gggttaacaa tcgaagtcat ggaatatgga tttggtccaa      1920
gattttccga gagctttcta gtagaaagcc catcaccaga aatttactag taaaataaat      1980
caccaattag gtttcttatt atgtgccaaa ttcaatataa ttatagagga tatttcaaat      2040
gaaaacgtat gaatgttatt agtaaatggt caggtaagac attaaaaaaa tcctacgtca      2100
gatattcaac tttaaaaatt cgatcagtgt ggaattgtac aaaaatttgg gatctactat      2160
atatatataa tgctttacaa cacttggatt ttttttttgga ggctggaatt tttaatctac      2220
atatttgttt tggccatgca ccaactcatt gtttagtgta atactttcat tttgtcaaat      2280
atatgtgttc gtgtatattt gtataagaat ttctttgacc atatacacac acacatatat      2340
atatatatat atatattata tatcatgcac ttttaattga aaaaataata tatatatata      2400
tagtgcattt tttctaacaa ccatatatgt tgcgattgat ctgcaaaaat actgctagag      2460
taatgaaaaa tataatctat tgctgaaatt atctcagatg ttaagatttt cttaaagtaa      2520
attctttcaa attttagcta aaagtcttgt aataactaaa gaataataca caatctcgac      2580
cacggaaaaa aaacacataa taaatttgaa tttcgaccgc ggtacccgga attcgagctc      2640
ggtacccggg gatcttcccg atctagtaac atagatgaca ccgcgcgcga taatttatcc      2700
tagtttgcgc gctatatttt gttttctatc gcgtattaaa tgtataattg cgggactcta      2760
atcataaaaa cccatctcat aaataacgtc atgcattaca tgttaattat tacatgctta      2820
acgtaattca acagaaatta tatgataatc atcgcaagac cggcaacagg attcaatctt      2880
aagaaacttt attgccaaat gtttgaacga tctgcttcgg atcctctaga gccggaaagt      2940
gaaattgacc gatcagagtt tgaagaaaaa tttattacac actttatgta aagctgaaaa      3000
aaacggcctc cgcaggaagc cgttttttc gttatctgat ttttgtaaag gtctgataat      3060
ggtccgttgt tttgtaaatc agccagtcgc ttgagtaaag aatccggtct gaatttctga      3120
agcctgatgt atagttaata tccgcttcac gccatgttcg tccgcttttg cccgggagtt      3180
tgccttccct gtttgagaag atgtctccgc cgatgctttt ccccggagcg acgtctgcaa      3240
ggttcccttt tgatgccacc cagccgaggg cttgtgcttc tgattttgta atgtaattat      3300
caggtagctt atgatatgtc tgaacataat ccgcaacccc gtcaaacgtg ttgataaccg      3360
gtaccatggt agctaatttc tttaagtaaa aactttgatt tgagtgatga tgttgtactg      3420
ttacacttgc accacaaggg catatataga gcacaagaca tacacaacaa cttgcaaaac      3480
taacttttgt tggagcattt cgaggaaaat ggggagtagc aggctaatct gagggtaaca      3540
ttaaggtttc atgtattaat ttgttgcaaa catggactta gtgtgaggaa aaagtaccaa      3600
aattttgtct caccctgatt tcagttatgg aaattacatt atgaagctgt gctagagaag      3660
atgtttattc tagtccagcc acccaccttta tgcaagtctg cttttagctt gattcaaaaa      3720
ctgatttaat ttacattgct aaatgtgcat acttcgagcc tatgtcgctt taattcgagt      3780
aggatgtata tattagtaca taaaaaatca tgtttgaatc atctttcata aagtgacaag      3840
tcaattgtcc cttcttgttt ggcactatat tcaatctgtt aatgcaaatt atccagttat      3900
```

```
acttagctag atatccaatt ttgaataaaa atagctcttg attagtaaac cggatagtga      3960
caaagtcaca tatccatcaa acttctggtg ctcgtggcta agttctgatc gacatggggt      4020
taaaatttaa attgggacac ataaatagcc tatttgtgca aatctcccca tcgaaaatga      4080
cagattgtta catggaaaac aaaaagtcct ctgatagaag tcgcaaagta tcacaatttt      4140
ctatcgagag atagattgaa agaagtgcag ggaagcggtt aactggaaca taacacaatg      4200
tctaaattaa ttgcattcgc taaccaaaaa gtgtattact ctctccggtc cacaataagt      4260 tatttttgg cccttttttt atggtccaaa ataagtgagt tttttagatt tcaaaaatga       4320
tttaattatt tttttactac agtgcccttg gagtaaatgg tgttggagta tgtgttagaa      4380
atgtttatgt gaagaaatag taaaggttaa tatgatcaat ttcattgcta tttaatgtta      4440
aaatgtgaat ttcttaatct gtgtgaaaac aaccaaaaaa tcacttattg tggaccggag      4500
aaagtatata aatatatatt tggaagcgac taaaaataaa cttttctcat attatacgaa      4560
cctaaaaaca gcatatggta gtttctaggg aatctaaatc actaaaatta ataaaagaag      4620
caacaagtat caatacatat gatttacacc gtcaaacacg aaattcgtaa atatttaata      4680
taataaagaa ttaatccaaa tagcctccca ccctataact taaactaaaa ataaccagcg      4740
aatgtatatt atatgcataa tttatatatt aaatgtgtat aatcatgtat aatcaatgta      4800
taatctatgt atatggttag aaaaagtaaa caattaatat agccggctat ttgtgtaaaa      4860
atccctaata taatcgcgac ggatccccgg gaattccggg gaagcttaga tccatgcaga      4920
tctgatcatg agcggagaat taagggagtc acgttatgac ccccgccgat gacgcgggac      4980
aagccgtttt acgtttggaa ctgacagaac cgcaacgatt gaaggagcca ctcagccgcg      5040
ggtttctgga gtttaatgag ctaagcacat acgtcagaaa ccattattgc gcgttcaaaa      5100
gtcgcctaag gtcactatca gctagcaaat atttcttgtc aaaaatgctc cactgacgtt      5160
ccataaattc ccctcggtat ccaattagag tctcatattc actctcaatc caaaccatga      5220
aaaaagcagt cattaacggg gaacaaatca gaagtatcag cgacctccac cagacattga      5280 aaaggagct tgcccttccg gaatactacg gtgaaaacct ggacgcttta tgggattgtc       5340
tgaccggatg ggtggagtac ccgctcgttt tggaatggag gcagtttgaa caaagcaagc      5400
agctcactga aaatggcgcc gagagtgtgc ttcaggtttt ccgtgaagcg aaagcggaag      5460
gctgcgacat caccatcata ctttcttaat acgatcaatg ggagatgaac aatatggaaa      5520
cacaaacccg caagcttggt ctagaggatc ccccgatgag ctaagctagc tatatcatca      5580
atttatgtat tacacataat atcgcactca gtctttcatc tacggcaatg taccagctga      5640
tataatcagt tattgaaata ttctgaatt taaacttgca tcaataaatt tatgtttttg       5700
cttggactat aatacctgac ttgttatttt atcaataaat atttaaacta tatttctttc      5760
aagatgggaa ttaacatcta caaattgcct tttcttatcg accatgtaca tcgagctctc      5820
cccagatctg catggagcca tttacaattg aatatatcct gccg                       5864
```